(12) United States Patent
Figiel

(10) Patent No.: US 6,567,720 B1
(45) Date of Patent: May 20, 2003

(54) METHOD AND APPARATUS FOR TIME SYNCHRONIZED MEASUREMENT CORRECTION OF MULTIDIMENSIONAL PERIODIC EFFECTS ON A MOVING WEB

(76) Inventor: Kerry D. Figiel, 4994 Barnsby La., Cincinnati, OH (US) 45244

( * ) Notice: Subject to any disclaimer, the term of this patent is extended or adjusted under 35 U.S.C. 154(b) by 257 days.

(21) Appl. No.: 09/839,980

(22) Filed: Apr. 20, 2001

(51) Int. Cl.$^7$ .................................................. G06F 7/66
(52) U.S. Cl. ........................ 700/129; 162/198; 162/263; 73/159
(58) Field of Search ................................ 700/127, 128, 700/129; 702/81; 162/198, 263; 73/159

(56) References Cited

U.S. PATENT DOCUMENTS

| | | |
|---|---|---|
| 3,622,448 A | 11/1971 | Adams et al. |
| 3,673,865 A | 7/1972 | Michaelsen |
| 3,794,427 A | 2/1974 | Shibata et al. |
| 3,840,302 A | 10/1974 | Brunton et al. |
| 3,936,665 A | 2/1976 | Donoghue |
| 3,989,085 A | 11/1976 | Crosby |
| 4,019,066 A | 4/1977 | Lucas et al. |
| 4,092,068 A | 5/1978 | Lucas et al. |
| 4,152,202 A | 5/1979 | DeLigt |
| 4,879,471 A | 11/1989 | Dahlquist |
| 4,903,528 A | 2/1990 | Balakrishnan et al. |
| 4,921,574 A | 5/1990 | Hu |
| 4,947,684 A | 8/1990 | Balakrishnan |
| 5,022,966 A | 6/1991 | Hu |
| 5,121,332 A | 6/1992 | Balakrishnan et al. |
| 5,122,963 A | 6/1992 | Chen |
| 5,125,746 A | 6/1992 | Lipshitz |
| 5,358,606 A | 10/1994 | Makkonen |
| 5,400,258 A | 3/1995 | He |
| 5,563,809 A | * 10/1996 | Williams et al. ............... 702/84 |
| 5,725,737 A | 3/1998 | Pikulik et al. |
| 5,745,365 A | 4/1998 | Parker |
| 5,960,374 A | 9/1999 | Lausier |

* cited by examiner

Primary Examiner—Leo Picard
Assistant Examiner—Alexander Kosowski

(57) ABSTRACT

An improved measuring system used with a process control system provides substantially real time correction of aliasing effects in a system having moving equipment that exhibits periodic parameters while being monitored. The measuring/control system can be used with a rotating equipment process line, such as used in a paper mill, in which a measurement scanner travels in the cross direction of a moving web of material, while that same moving web of material continues to move in a longitudinal direction (the machine direction) transverse to the cross direction. The measuring/control system begins by acquiring data utilizing a time synchronous monitoring system that produces a count matrix and a measurement matrix of readings from the measurement scanner. After a sufficient number of data samples have been acquired, a correction matrix can be built. Each sample of data can be adjusted for the contribution of each of the rotating elements at the data processing level before the raw reading is processed into a measurement or a profile. In this manner, the aliasing effect of all mapped rotating elements can be removed from the measurement. The output measurement matrix element values are converted by the measuring/control system to deviations from the average, caused by each rotating element. These values are then used by a correction algorithm. Each rotational element has its own correction map generated, and the CD position of the scanner is known at each data collection interval, and further the rotational position of each rotating element is also known at each data collection interval. The measuring/control system can use these raw sensor readings and correct them for each CD and MD positional effect, or for each rotational element. The measuring/control system can provide immediate correction for rotational effects at the time of sampling, before the data is averaged or used in any other way. This permits the rotational effects of multiple rotating elements to be removed deterministically in real time.

42 Claims, 9 Drawing Sheets

FIG. 5 EXAMPLE GRAPHICAL/PROFILE DATA

METHOD AND APPARATUS FOR TIME SYNCHRONIZED MEASUREMENT CORRECTION OF MULTIDIMENSIONAL PERIODIC EFFECTS ON A MOVING WEB

TECHNICAL FIELD

The present invention relates generally to process control lines such as paper manufacturing equipment and is particularly directed to paper machines of the type which transport webs of paper fibers that are being formed into rolls of finished paper. The invention is specifically disclosed as a method for real time correction of measurements of process variables which, without correction, are manifested as cross direction and machine direction variability in the paper web due to rotating or periodic equipment by use of a time synchronized measurement correction technique.

BACKGROUND OF THE INVENTION

Computerized monitoring systems have been used to monitor the properties of a moving web of material such as that produced in paper mills. In such systems, the process variables that are monitored relate to the "machine direction" (MD) or the "cross direction" (CD), and some process variables are related to physical parameters that are affected in both directions.

One of the problems in the current state of control technology is the limited ability to separate true cross direction variability (which is positionally dependent) from both machine direction variability (which is time dependent) that occurs uniformly across an entire moving web of material, and the effects of rotating equipment which produce machine direction variability that is positionally dependent. One current solution to this limitation is the use of filtering, however, this slows the speed of response of CD control, and sometimes cannot adequately resolve the true profile shape of the web.

The above filtering solution that is currently in use has a limitation because the filtering slows the speed of response of the CD control system. Moreover, the filtered results are not always able to adequately resolve the true profile shape. This is caused by inadequate sampling of the impact of the rotating or periodic equipment, and in certain cases the existence of a synchronization pattern between this equipment and the scanning measurement. A near exact synchronization produces an effect that can be referred to as an "aliased profile," in which the alias forms a false profile that is due to sampling the equipment repeatedly at the same position in its periodic cycle.

A breakthrough occurred with the ability to acquire on-line measurements and generate a time-synchronous array map of the moving web while in production, and this array or map can be used to assess the impact of the periodicity of the machine elements. This invention is disclosed in U.S. Pat. No. 5,960,374, titled "System for Time Synchronous Monitoring of Product Quality Variable," issued to Lausier on Feb. 14, 1997. The Lausier system builds count maps and measurement maps from a predetermined number of rotating elements. A scanning measurement frame is mounted across the width of the moving product web and takes on-line measurements of a selected variable in the cross direction and machine direction of the web. Event trigger signals from the sensors are coupled to elements of the process line, and the CD and MD measurements from the scanning sensors in a particular measurement frame are provided to the computer system. Data measurement "boxes" are used to receive the scanned measurements of paper quality variables (in the case of a paper mill) over the surface of the web, in which there are spatial CD zone increments and MD position/slash time increments that define the data measurement boxes. Given a sufficient amount of time and samples taken, the effect of all mapped rotating elements can be determined.

An example of the synchronization pattern referred to above is illustrated in FIG. 5, which depicts the count matrix comprising the number of scanned measurements that occurred when the coating rod was at each rotational position and the scanner was at each cross directional position. With perfect sampling, one would expect the same number of counts in each measurement cell. However, as can be seen on FIG. 5, some of the measurement cells are not sampled at all, while others were sampled over 180 times during the time interval during which samples were taken. Consequently, the value of the measurement cells in the heavily sampled regions will dominate the calculated values, and will falsely bias the profile estimation. This sampling error is not random, but appears in diagonal or cross-hatched patterns. In one process equipment installation, the cross-hatched pattern was produced by an almost exact 10:1 ratio between the scanner pattern and rod rotation period.

SUMMARY OF THE INVENTION

Accordingly, it is a primary advantage of the present invention to correct the measurement profile of a processing line of periodically-moveable equipment, such as rotating equipment, with little or no filtering. It is another advantage of the present invention to remove aliasing effects in substantially real time while measurements are being collected for a process line utilizing rotating equipment, such as used in a paper mill. It is a further advantage of the present invention to create accurate profiles of rotating equipment process lines that can be used for cross machine control with little or no filtering to provide immediate correction for rotational effects at the time of sampling and before the data is averaged or used in other ways, thereby allowing the control system to more quickly compensate for process line product changeovers or other variations in system components.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, an improved computerized process control system is provided that includes a process equipment line having at least one moving element that moves with a time periodicity that may vary for successive cycles of movement, which is used to produce a material which, for at least one stage of production, forms a moving web of material that is proximal to one or more of the moving element(s); a memory circuit for storing information, at least one input device that measures at least one process parameter of the moving web of material and associates that measurement with its multidimensional position on the web, and a processing circuit that controls a flow of information between the memory circuit and the input device(s); a sensor to determine the position of the periodic element; the processing circuit is configured to receive data from the input device(s) by measuring and numerically quantifying the at least one process parameter during multiple cycles of movement of the at least one moving element(s) and store the numerically quantified information in the memory circuit, then to build at least one Correction Map containing the numerically quantified information acquired over a predetermined time interval and to store the Correction Map in the memory circuit; and the processing circuit is further configured to, during a manufacturing operation, (i) again measure and numerically quantify the process parameter in substantially real time, (ii) determine positions of the moving element(s), (iii) apply the Correction Map(s) to the process parameter that is measured in substantially real time to generate at least one decoupled sample of the process parameter and store the decoupled sample(s) in the memory circuit; (iv) and utilize the decoupled sample(s) of the process parameter to operate the process equipment line, thereby providing a substantially real time measurement correction of product quality variability in the process equipment line.

In accordance with another aspect of the present invention, a method for substantially real time measurement correction of product quality variability in a process equipment line is provided, in which the method comprises: providing a process equipment line having at least one moving element that moves with a time periodicity that may vary for successive cycles of movement, and providing a moving quantity of material that is produced using the at least one moving element(s); providing a processing circuit, a memory circuit to store data, and at least one input device that measures at least one process parameter of the moving material; during multiple cycles of movement of the moving element(s), measuring and numerically quantifying the process parameter, then building at least one Correction Map containing the numerically quantified information acquired over a predetermined time interval; during a manufacturing operation, (i) again measuring and numerically quantifying the at least one process parameter in substantially real time, (ii) determining positions of the moving element(s), (iii) applying the Correction Map(s) to the process parameter that is measured in substantially real time to generate at least one decoupled sample of the process parameter; (iv) and utilizing the decoupled sample(s) of the process parameter to operate the process equipment line.

In accordance with a further aspect of the present invention, a computerized method for building a Correction Map for use in a system is provided including at least one rotating element having an associated moving web of material, in which the method comprises: sampling physical data by use of at least one input device that measures at least one process parameter of the moving web of material; determining a rotational position of each sample for each of the rotating element(s) that is/are being monitored; determining a cross-directional position of each sample of the physical data; updating a Sum Map and a Count Map for each of the rotating element(s), using the sampled physical data; determining if a sufficient amount of sampled physical data has been acquired for convergence to an appropriately small tolerance and, if NO sampling further physical data, or if YES building an Average Map for each of the at least one rotating element(s); and building a Correction Map for each of the rotating element(s), the Correction Map containing a plurality of numeric values related to irregularities in the rotating element(s).

In accordance with a still further aspect of the present invention, a computerized method for controlling in substantially real time a system is provided including at least one rotating element having an associated moving web of material, in which the method comprises: providing a control system for controlling the rotating element(s); providing a Correction Map for each. of the rotating element(s); acquiring a plurality of physical data samples by use of at least one input device that measures at least one process parameter of the moving web of material; determining rotational positions for each of the rotating element(s) that is/are being monitored, for each of the plurality of physical data samples; determining a cross-directional position of each sample of the physical data; by use of the Correction Map, looking up a correction value for each of the rotating element(s); generating rotationally decoupled values in substantially real time by applying the correction value to one of the plurality of physical data samples; and applying the rotationally decoupled values to the control system.

In accordance with yet another aspect of the present invention, a method for correction of product quality variability of a moving web of material in a process equipment line is provided, in which the method comprises: providing a process equipment line having at least one moving element that moves with a time periodicity that may vary for successive cycles of movement, and providing a moving web of material that is produced using the moving element(s); providing a processing circuit, a memory circuit, and at least one input device that measures at least one process parameter of the moving web of material; during multiple cycles of movement of the moving element(s), measuring and numerically quantifying the process parameter, then building a Correction Map containing the numerically quantified information acquired over a predetermined time interval; determining, for each web cross direction position, a correction for non-uniformity in a Count Map, for all of the moving element(s); creating a Correction Profile by summing, for each web cross direction position, the corrections for all of the moving element(s); creating a Measured Profile by averaging samples of the numerically quantified information taken at each cross direction position over the predetermined time interval; creating a True Profile by subtracting the Correction Profile from the Measured Profile; determining a True Machine Direction Average by adding weighted cross direction positions of the True Profile; and controlling the process equipment line using the True Profile and the True Machine Direction Average as corrected values.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE PREFERRED EMBODIMENT

Figure 1:
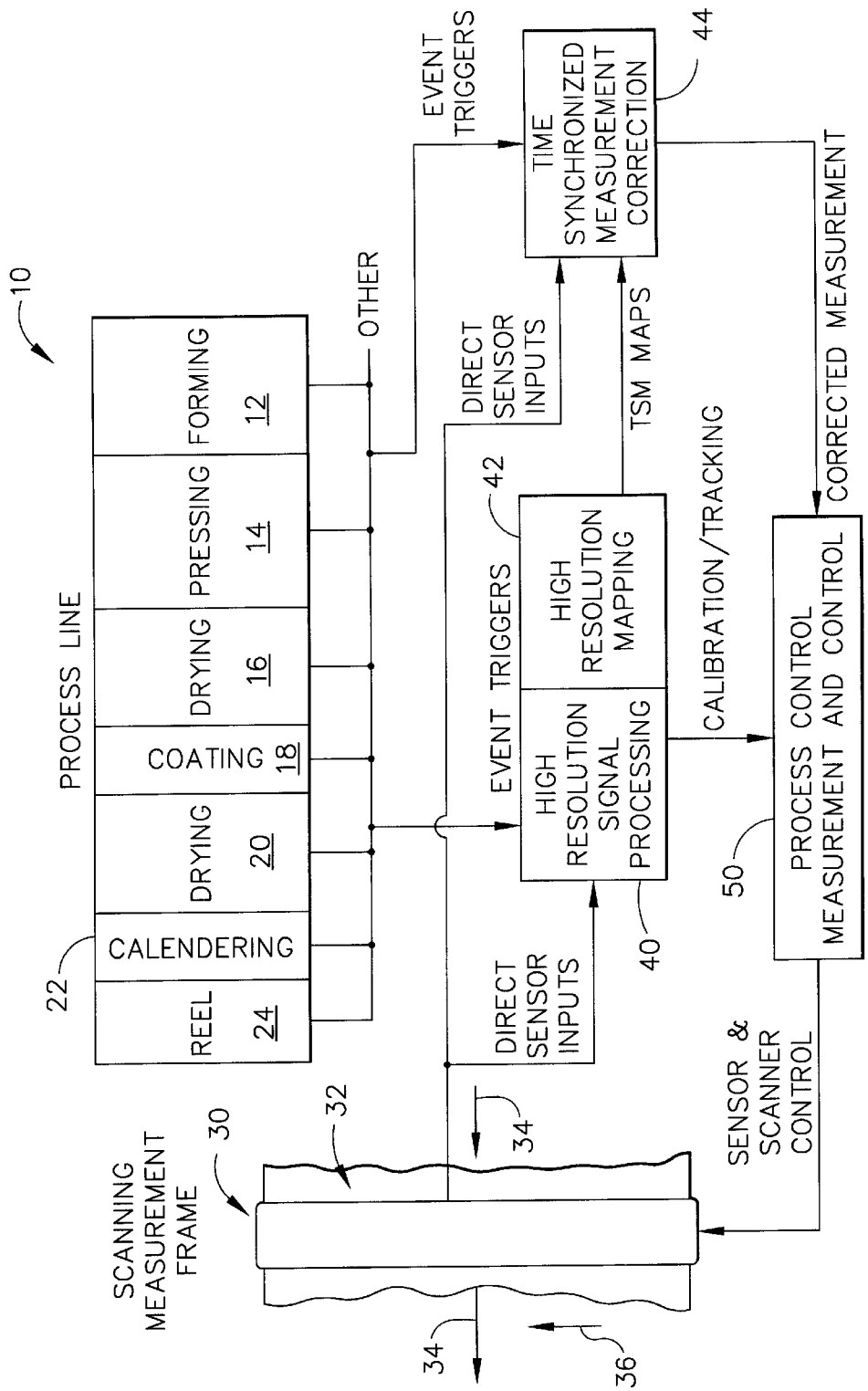
FIG. 1 is a diagrammatic view showing the general layout of a process control line for manufacturing paper which monitors product quality, as according to the present invention.

Reference will now be made in detail to the present preferred embodiment of the invention, an example of which is illustrated in the accompanying drawings, wherein like numerals indicate the same elements throughout the views.

An improved process line control system is provided that provides substantially real time correction of sampling errors in a system having moving equipment that exhibits periodic parameters while being monitored. Specifically, the present invention can be used with a rotating equipment process line, such as used in a paper mill, in which a measurement scanner travels in the cross direction of a moving web of material, while that same moving web of material continues to move in a longitudinal direction that is transverse to the cross direction. This longitudinal direction is also known as the machine direction, and typically follows the path of the moving web of material between rolls or reels, or other types of rotating equipment. The process control system of the present invention begins by acquiring data utilizing a time synchronous monitoring system that produces a count matrix and a measurement matrix of readings from the scanner described above. After a sufficient number of data samples have been acquired, a Correction Map can be generated which describes the measurement error caused by the rotating (periodic) equipment for every cross machine and machine direction position.

Rather than using filtering to remove high frequency variability over relatively long time durations, the raw measurement is corrected using the present invention in substantially real time without this time filtering. Since the measurement maps are quite stable over useful time periods (such as days or months), they can be used as an adjustment to the instantaneous measurement. Each sample of data can be adjusted for the contribution of each of the rotating elements at the data processing level before the raw reading is processed into a measurement or a profile. In this manner, the effect of nonuniform sampling of all mapped rotating elements can be removed from the measurement.

As described above, cross direction profiles are normally highly filtered to remove high frequency variability in conventional cross machine control systems. One of the sources of this high frequency variability is the rotational effect of rolls, rods, felts, drums, wires, etc. on the paper process control system. Consequently, even when there is no exact synchronization or an alias, these rotational effects can interfere with the measurement. Since filtering produces a time lag before the process control system can begin to accurately correct its outputs, a correction of the profile without the use of filtering is a much more desirable option. The count maps and measurement maps produced by the conventional time synchronous monitoring system are utilized as the beginning point of the present process control system. Since the present invention corrects in substantially real time for errors in the sensor measurements based upon maps from the time synchronous monitoring system, the present invention is also referred to as a "time synchronized measurement correction system."

The output measurement matrix derived from the conventional time synchronous monitoring system provides a sensor measurement value associated with each measurement cell. These values are converted by the present invention to deviations from the average, caused by each rotating element. These values are then used by a correction algorithm. Assuming that the time synchronous monitoring system is simultaneously used on "n" elements and that each rotational element has its own correction map that has been generated, then the CD position of the scanner is known at each data collection interval, and further the rotational position of each rotating element is also known at each data collection interval. The present invention can use these raw sensor readings and correct them for CD and MD positional effects for each rotational element.

As an example, if n rotating elements are being synchronized and a conventional time synchronous monitoring system is used to generate maps, then these maps can be used to generate a correction value for the time synchronized effect at every later sample. If there are "k" rotational elements, and they are in a particular rotational position "i" and cross direction position "j" at the time the sample is acquired, then a correction matrix can be described as $C_{ijk}$ for all readings "X" that are collected. A time synchronized measurement correction is given the designation "Y." The appropriate equation is as follows:

$$Y = X - \sum_{k=1}^{n} C[i_k j_k k]$$

where $i_k$ is the current rotational position for element k, and $j_k$ is the current cross direction position for element k.

As described above, the aliases between scanners and rotating elements can be highly stable, but such aliases will not be adequately corrected using existing filtering techniques. The present invention can provide immediate correction for rotational effects at the time of sampling and before the data is averaged or used in any other way. This permits the rotational effects of multiple rotating elements to be removed deterministically in real time.

The present invention can also be used in alternative configurations such as developing a correction map by techniques other than the use of a time synchronous monitoring system. The correction of a single-dimensional data (such as time) can be accomplished without any cross directional component. Another alternative system is the correction of three-dimensional data if a scanning sensor is used that can measure variations in properties at various sheet depths, for example the sheet moisture content at various depths in the sheet. Another alternative embodiment would be to incorporate the present invention as an error correction system used in an existing conventional time synchronous monitoring system, while sharing the same triggers and process inputs.

A list of definitions for certain common terminology used herein will now be provided to more readily make clear the principles of the present invention. These definitions immediately follow below:

Machine Direction (MD): In a process where a sheet (or web) is produced, the machine direction is the surface direction in which the sheet is being transported.

Cross Direction (CD): In a process where a sheet (or web) is produced, the cross direction is the surface direction perpendicular to sheet movement. Also called Cross Machine.

Element (or Rotating Element): These are devices that have a periodic frequency associated with them that may affect the property measured by the sensor. These devices may rotate in the direction of the two-dimensional sheet (e.g., a roll) or create a movement in the cross direction (e.g., an oscillating shower).

Sensor: This is a device that measures a property of the two-dimensional sheet in real-time. Real-time means that the measurement is made in the production system as the sheet is being run and is not a lab measurement conducted off-line and outside of the production system.

Scanner: A scanner is a device composed of a frame and a moving carriage. The frame runs across the width of the sheet and guides the movement of the carriage. The carriage rides on the frame and transports sensors across the sheet to collect measurements.

Profile: A profile is a measurement (estimate) of the cross-directional changes in properties. It is a graph with the scanner property measurement on the vertical axis and cross-directional position on the horizontal.

Single Scan (or Raw) Profile: This is a profile resulting from a single traverse of the scanner across the sheet. The properties measured on the vertical axis are a sum of the true cross-directional properties and any machine directional variations that occurred while the scanner moved across the sheet.

Filtered (or Multi-scan) Profile: This is a profile estimate in which mathematical techniques have been employed to remove or reduce machine direction variations so that the true cross-directional properties are displayed. Common mathematic techniques include arithmetic averaging and exponential filtering.

Map: A two-dimensional matrix in which the axes (rows and columns) are the independent values and the cell values are the dependent values.

Referring now to the drawings, FIG. 1 illustrates in block diagram form a process line used in a paper mill that includes a process control monitoring and control system. Many of the components illustrated on FIG. 1 are described in U.S. Pat. No. 5,960,374, which as noted above was issued on Feb. 14, 1997 to Lausier, and which is assigned to International Paper Company and is incorporated herein by reference in its entirety. A conventional paper process line generally represented by the reference numeral 10 includes a paper web forming section 12, a pressing section 14, a drying section 16, a coating section 18, a secondary drying section 20, a calendering section 22, and a windup reel section 24. Sensors coupled to machine elements of the process line are used to provide event trigger signals that are indicative of the operational condition of the element being monitored. Event trigger signals are preferably provided to indicate the periodicity of one or more machine elements. Magnetic or photoelectric sensors may be used to detect the passage of a marker that is coupled to the moving machine element to demarcate each cycle or revolution of a rotational element being monitored.

A scanning measurement frame 30 is mounted across the width of a moving product web 32, and provides on-line measurements of a selected variable in the cross direction (CD) and machine direction (MD) of the web 32. In the representation of FIG. 1, the MD is illustrated at the arrow 34, and the CD is illustrated at the arrow 36.

The event trigger signals from the sensors that are coupled to elements of the process line 10 and the CD/MD measurement inputs from the scanning sensors of the measurement frame 30 are provided to a computer system that includes a high resolution signal processing front end 40, and a high resolution mapping module 42. These direct sensor inputs are also provided to a time synchronized measurement correction module 44, as are the event triggers. In addition, the measurement maps and count maps (referred to together as "TSM maps") are also provided to the time synchronized measurement correction module 44 from the high resolution mapping module 42.

Sensor calibration is verified and adjusted on a frequent basis within control section 50. Both modules 40 and 44 must track these calibration changes to properly convert signals to their correct engineering values. This process and measurement control section 50 is also used to control the scanning sensors or scanning functions, and/or the process line elements or their functions, based upon analyses of the paper quality measurement data. The corrected measurements are then sent back to control section 50 to be used in real-time control and displays.

In a typical paper process line, the web CD/MD measurements are preferably sampled at a rate greater than 150 samples per second. Each scanning measurement is identified with an MD and CD tag. The scanning device of the scanning measurement frame 30 may be mechanical, optical, or electronic. The CD/MD measurement data captured by the signal processing front end 40 are then processed into array maps of the selected paper quality variable by the mapping module 42, based upon their MD and CD coordinate tags. The same measurement data may be associated with multiple maps, or combined with other measurement data to generate other maps. Multiple paper quality variable maps can be built simultaneously.

Figure 2:
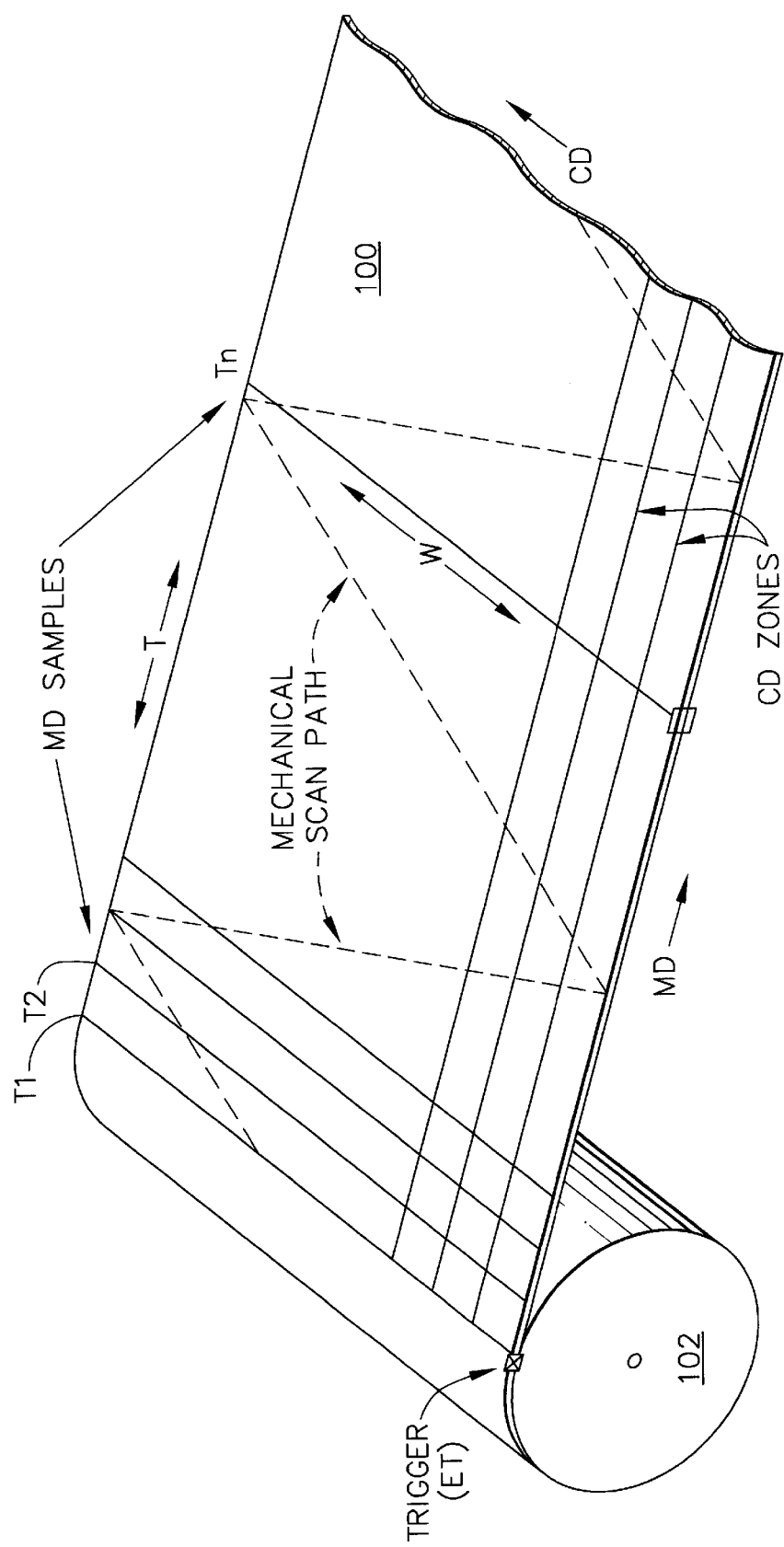
FIG. 2 is a perspective view of a portion of the process control line of FIG. 1, and illustrates how CD and MD position increments are defined for use in identifying CD/MD measurement boxes.

The measurement frame 30 can include an array of sensors arranged in rows across the width of the web 32, or a sensor device can be mechanically shuttled or optically scanned across the web from side to side continuously. A web line may have a number of scanners to obtain essential measurements at different critical points in the processing line. If the scanner uses a mechanically shuttled or traversed sensor, the scanner position measurements must also be taken since they are essential to controlling the scanner within the physical limits of the web and to properly tag the measurement data with accurate coordinates. The CD profiles of the measurement data are generated with the use of scanner position measurements. The CD coordinate is position based (spatial), which preferably is based upon an increment of the width of the web. On FIG. 2, the width of the web 100 is designated by the letter "W," and can be divided into a plurality of CD zones. Measurements may be taken by a sensor array with elements positioned at the CD zone increments, or by scanning a sensor device from side-to-side across the mechanical scan path, as indicated on FIG. 2.

The MD position is preferably selected as increments of running distance corresponding to an increment of the time periodicity of a machine element being monitored. Event triggers are mounted on each machine element being monitored, such as the roll 102, and are used to signal each detected cycle or a complete rotation of the element. The time period of the element is divided into time increments which are used to define the MD position coordinates for the measurement data boxes that will be used to contain the data.

Each MD data box is represented by an MD position at a time interval, referenced from the event trigger signal. The running length of the web in the MD corresponding to the time period "T" defined by the trigger "ET" (see FIG. 2) is divided into time increments T1, T2, ..., Tn. The spatial CD zone increments and the MD position/time increments together define the data measurement boxes that are filled with information from the scanned measurements of the measured paper quality variable over the surface of the web. These CD/MD measurement data boxes provide the data elements from which an array mapping of the paper quality variable can be built, referenced to the MD and CD coordinates.

Figure 3:
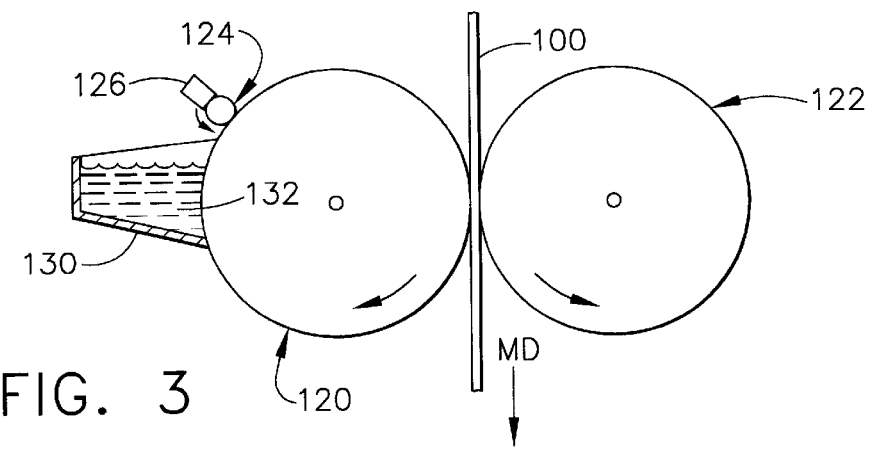
FIG. 3 is an elevational view in cross-section of a coating station which could be used in the process control line illustrated in FIG. 1.

FIG. 3 illustrates an example coating station used on a paper processing line, such as the coating station 18 depicted on FIG. 1. A moving web of paper material 100 is travelling in the machine direction through a nip between two backing rolls 120 and 122. A trough-like structure at 130 contains a coating material 132, and is positioned such that the coating material 132 makes contact with the outer surface of the cylindrical backing roll 120. As the roll 120 rotates, some of the coating material 132 will adhere to its surface and travel along that cylindrical surface toward the moving web of paper material 100.

Figure 4:
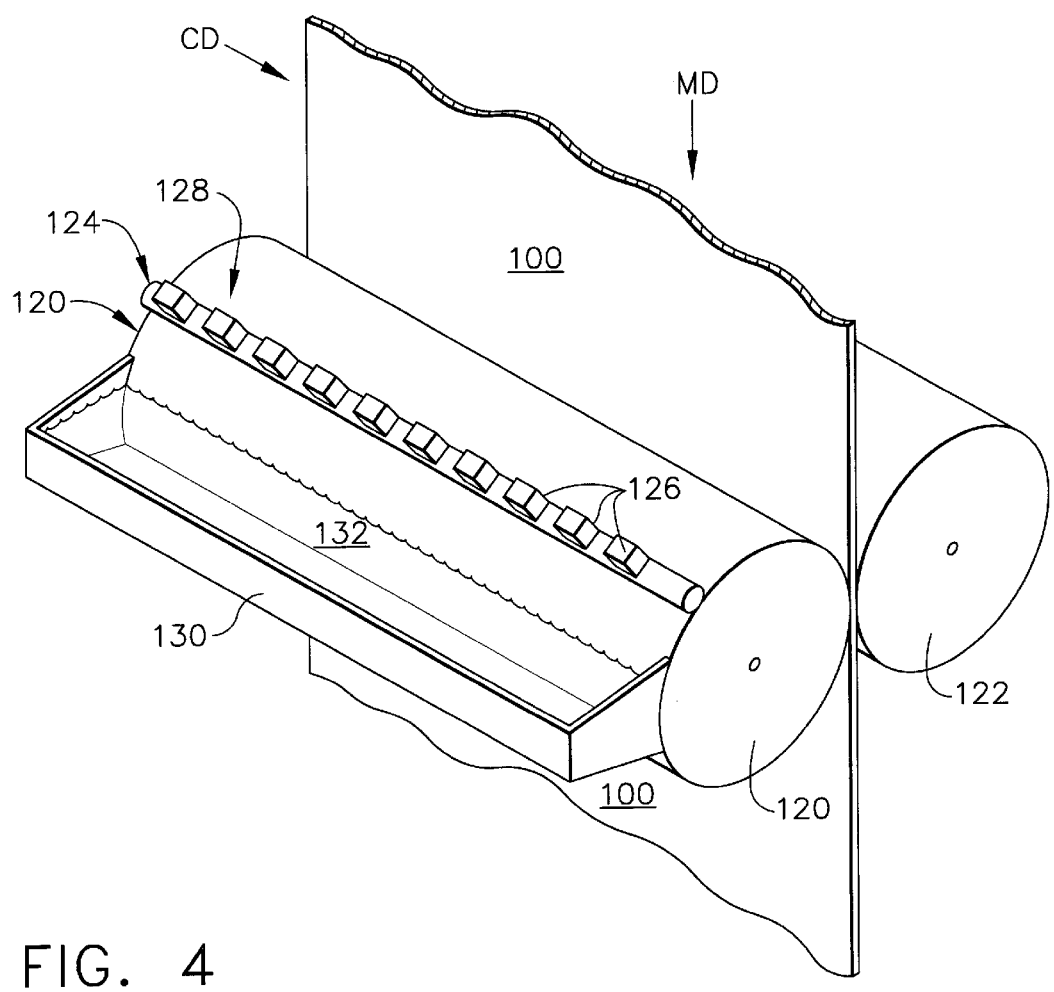
FIG. 4 is a perspective view of the coating station of FIG. 3.

A "top rod" 124 is positioned very close to the cylindrical surface of the backing roll 120, and is used to control the amount of coating material 132 that is spread along the surface of the backing roll 120. On FIG. 4, the coating material 132 adheres to the outer surface of the backing roll 120 and travels along that surface at the area designated by the reference numeral 120. However, the amount of coating material is reduced (or at least controlled) by the top rod 124, so that when the coating material travels past top rod 124 while still adhering to the surface of the backing roll 120 in the area designated by the reference numeral 128, the amount of coating material will be substantially reduced in most situations.

Several controllable actuators 126 are used to press against the top rod 124 at intervals along the cross direction of top rod 124. This is easily seen in the perspective view of FIG. 4. In a typical installation of a process line paper mill, the actuators 126 would be spaced apart from one another by about four inches (10 cm). One of the important functions of the process control system 50 is to provide a substantially even coating on the moving web of paper material 100, and this is accomplished by properly causing the multiple actuators 126 to apply individual amounts of force, such that the coating material 132 will not be too thick or too thin at certain locations along the cross direction. It will be understood that the actuators 126 are generally individually controllable, although in some installations there could be some combination of actuators that could be controlled in groups.

Other types of cross-machine actuators can be used, such as water spray equipment that may be used in the drying stage of the process line, such as the drying stage 16 on FIG. 1. Another example actuator is a set of individual heating elements at various locations in the cross direction that could be used in the calendaring stage 22, as depicted in FIG. 1. These types of actuators or process variable controllable transducers are well known in the art, and virtually any type of actuator or sensor can be controlled and read by the process control system 50 of the present invention.

Using the information gathered by the signal processor unit 40 and the high resolution mapping unit 42 of the time synchronous monitoring system as taught in U.S. Pat. No. 5,960,374, a count map can be generated, such as that depicted in FIG. 5. This count map is based upon a test run of a paper process line using a scanning measurement frame in which there was an almost exact 10:1 ratio between the scanner period and the rod rotation period.

Figure 5:
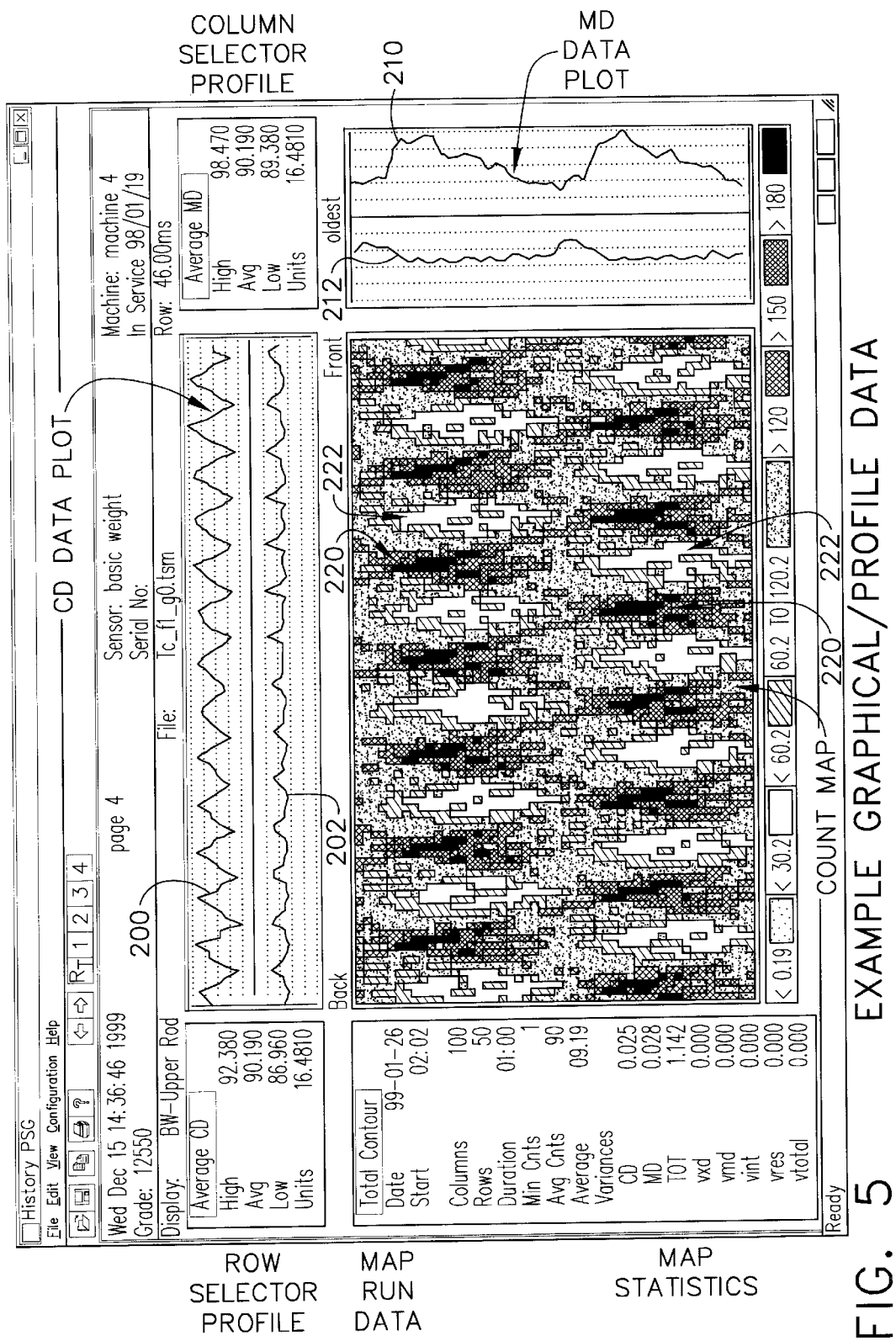
FIG. 5 is a representation of a computer monitor screen that displays in color a Count Map, CD data plot, and MD data plot, all in graphical form.

The number of measurements taken in the machine direction and cross direction of the moving web can be plotted using the count map measurement boxes, and this plot is depicted in the main portion of the displayed information on FIG. 5. This displayed information is an example of a computer monitor display screen that can be generated using the principles of the present invention. If the sampling were perfect, then each x-y coordinate on the count map would have an identical number of readings taken. However, the sampling is not perfect, and it can be seen that some cells were sampled very little or not at all, while other cells were sampled over 180 times. The highly sampled areas are designated at the reference numerals 220 by darkened symbols, while the areas that were barely sampled at all (e.g., less than 30 samples) are designated at the reference numerals 222 by "white" or clear areas. As can be easily seen in FIG. 5, the sampling error is not random, as discussed hereinabove, but has the appearance of diagonal shapes producing cross-hatched patterns.

FIG. 5 also illustrates certain other process parameter information, including a row selector profile, map run data, map statistics, and a column selector profile. Furthermore, two other graphs are illustrated on FIG. 5.

The first other graph is a Cross Direction Plot which illustrates the measured process variable (or counts) versus CD position, and produces an envelop plot of the maximum (200) and minimum (202) values in each column. In addition, an average of the Cross Direction Plot is also graphed, and is illustrated at 201.

In a similar manner, a Machine Direction Envelop Plot is illustrated and shows the measured process variable (or counts) of the periodic element versus the MD time position. The raw data plot is graphically depicted at the curve 210, while an average of this curve is depicted at 212.

Figure 6:
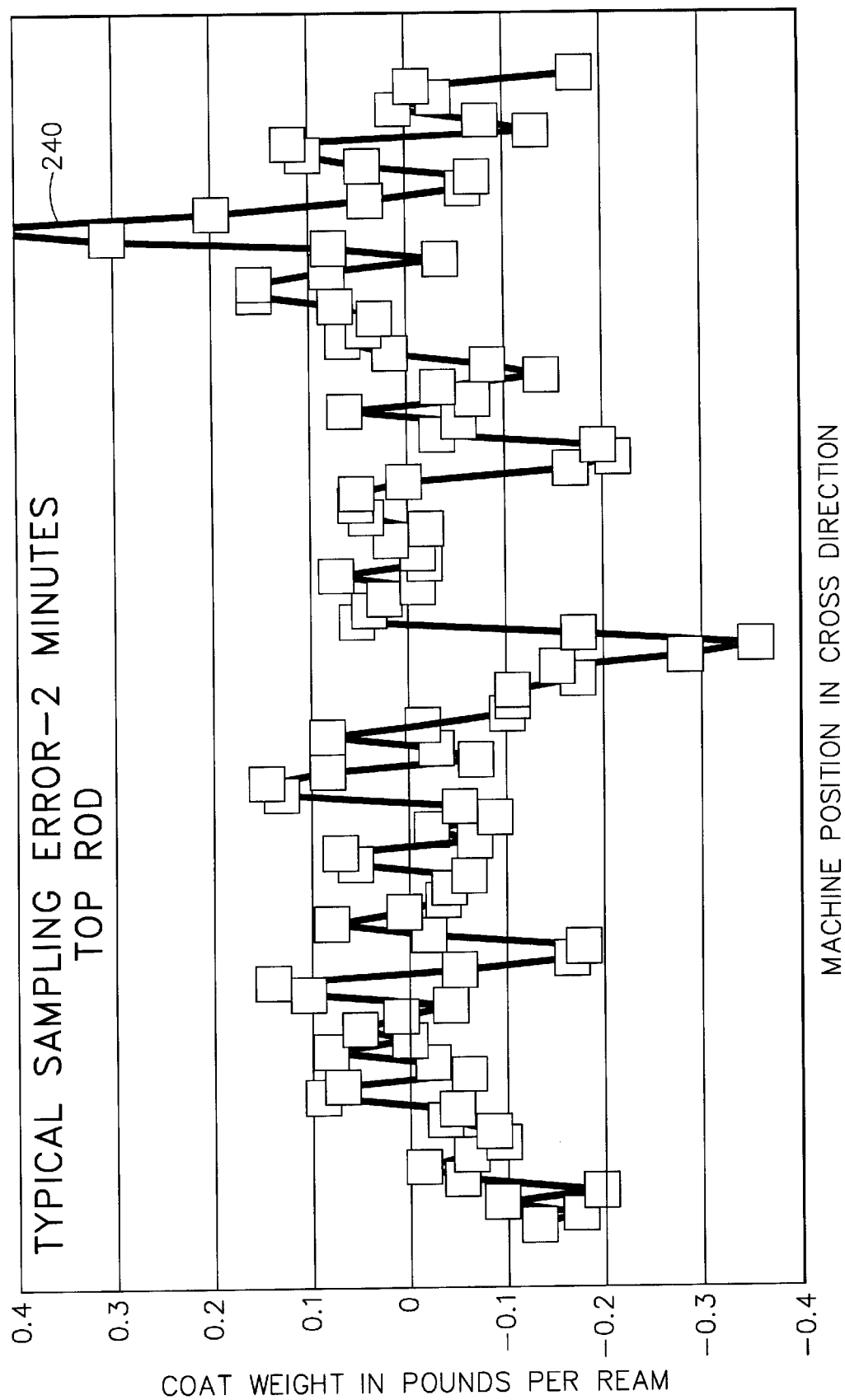
FIG. 6 is a graph illustrating calculated measurement error of a process variable in which the information was acquired using CD/MD measurement boxes.

By using the count maps and measurement maps produced by the signal processing and mapping elements 40 and 42 of the time synchronous monitoring system, the average measurement error can be calculated using the principles of the present invention as described in greater detail below. In general, this is accomplished by weighting a measurement by an amount of time that the reading occurred at various locations in the matrix or map. An example of a calculated measurement error plot is illustrated in FIG. 6, in which a curve 240 indicates typical sampling error in the top rod of the coat weight versus the CD machine position.

Figure 7:
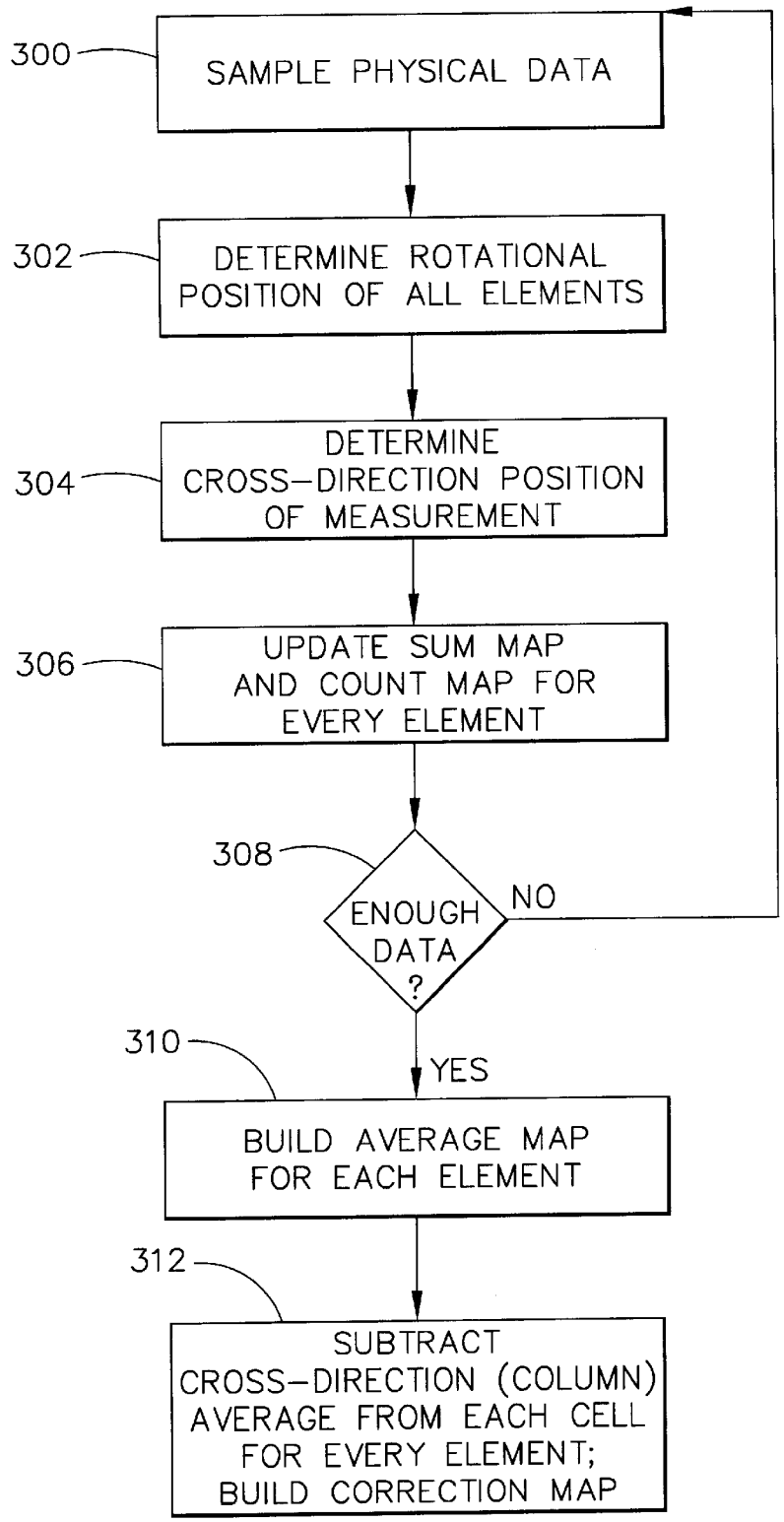
FIG. 7 is a flow chart of some of the important steps performed to build a Correction Matrix, as according to the principles of the present invention.

FIG. 7 is a flow chart that describes the important functional steps in building a "correction matrix" or "correction map." Starting at a step 300, the physical data is sampled by using sensors that measure the properties of the two-dimensional sheet or web of material. These measurements are converted into discrete samples of data at a relatively fast collection speed. By "relatively fast," this means that the samples are gathered quickly with respect to movements of the rotating machine elements of the process line.

At a step 302, the rotational position of all elements that are being analyzed in the process line 10 are determined. The rotational elements that may affect the measured property (i.e., the process variable being inspected) must be identified in advance and instrumented. Although many techniques may be used to accomplish this measurement, the rotational position ultimately must be converted to one of the independent axes of the maps. If "m" rotational positions are used in the map, then the rotational position of each element must be converted to a number from 1 to m.

A step 304 now determines the cross-direction position of the measurements. Each sensor measurement is associated with a CD position on the sheet or web of moving material. If the CD axis on the map is broken into "n" positions, the CD position must be converted to a number from 1 to n.

Prior to the start of building a correction matrix (or "correction map"), every measurement cell of the Sum and Count Maps for all elements are initialized to zero (0). When a sample of physical data is collected, the Sum Map cell associated with the rotational and CD position is incremented by the value of the measurement. The Count Map cell associated with the same position is also incremented by one. This occurs at a step 306, in which the Sum Map and Count Map are updated for every element. A decision step 308 determines at this time if enough data has been gathered. In the setup of the time synchronous monitoring system, testing is conducted to determine the time that it takes for the Average Maps to converge to a stable map with each cell being within a certain tolerance of the true (or infinite collection time) value. When the current collection exceeds this time, enough data has been gathered to build a good Average Map. If that has occurred, then the YES result is the output of decision step 308. Otherwise the NO result is reached, and the logic flow travels back to step 300.

It will be understood that the term "Correction Map" can encompass forms of data other than a "map" or a "matrix" of numeric elements. For example, the Correction Map could merely be a grouping of data information that is stored in memory in linear form, in string form, or perhaps in a database format, or even perhaps in a spreadsheet program data set. Such numeric data could be operated on by various types of mathematical or logical functions, as required for the purposes of the present invention, including spreadsheet operators, or even Boolean operators in some circumstances. Moreover, such data can also be referred to as a "correction function" to more generalize its purpose in relation to the present invention.

However, for the purposes of clarification, this patent document will typically refer to this type of data as a "map." In a similar fashion, the other "maps" described herein could also be thought of in the general case as consisting of any form of numeric or alphanumeric data, and could be operated on by various types of mathematical or logical functions.

A step 310 now builds an Average Map for each element, by dividing each measurement cell of the Count Map into its corresponding cell of the Sum Map. Each measurement cell is the average value of the physical property associated with a certain cross machine position and rotational position of that element. The effect of all other elements are averaged out (or filtered) by a suitable long collection. In the general case, the "Average Map," "Sum Map," and "Count Map" could be referred to as an "average function," "sum function," and "count function," and could consist of data other than in a "map" or "matrix" format. As noted above, such maps or data sets could be operated upon by various mathematical or logical functions, without departing from the principles of the present invention.

A step 312 now subtracts the cross-direction (column) average from each cell for every element to build a Correction Map. The subtraction step creates a Correction Map that describes the impact of the element on the sampled physical data. If the cell corresponding to the current rotational position and the cross directional position is subtracted from the current sampled physical data, the resultant value is corrected for the rotational effect of the element.

Figure 8:
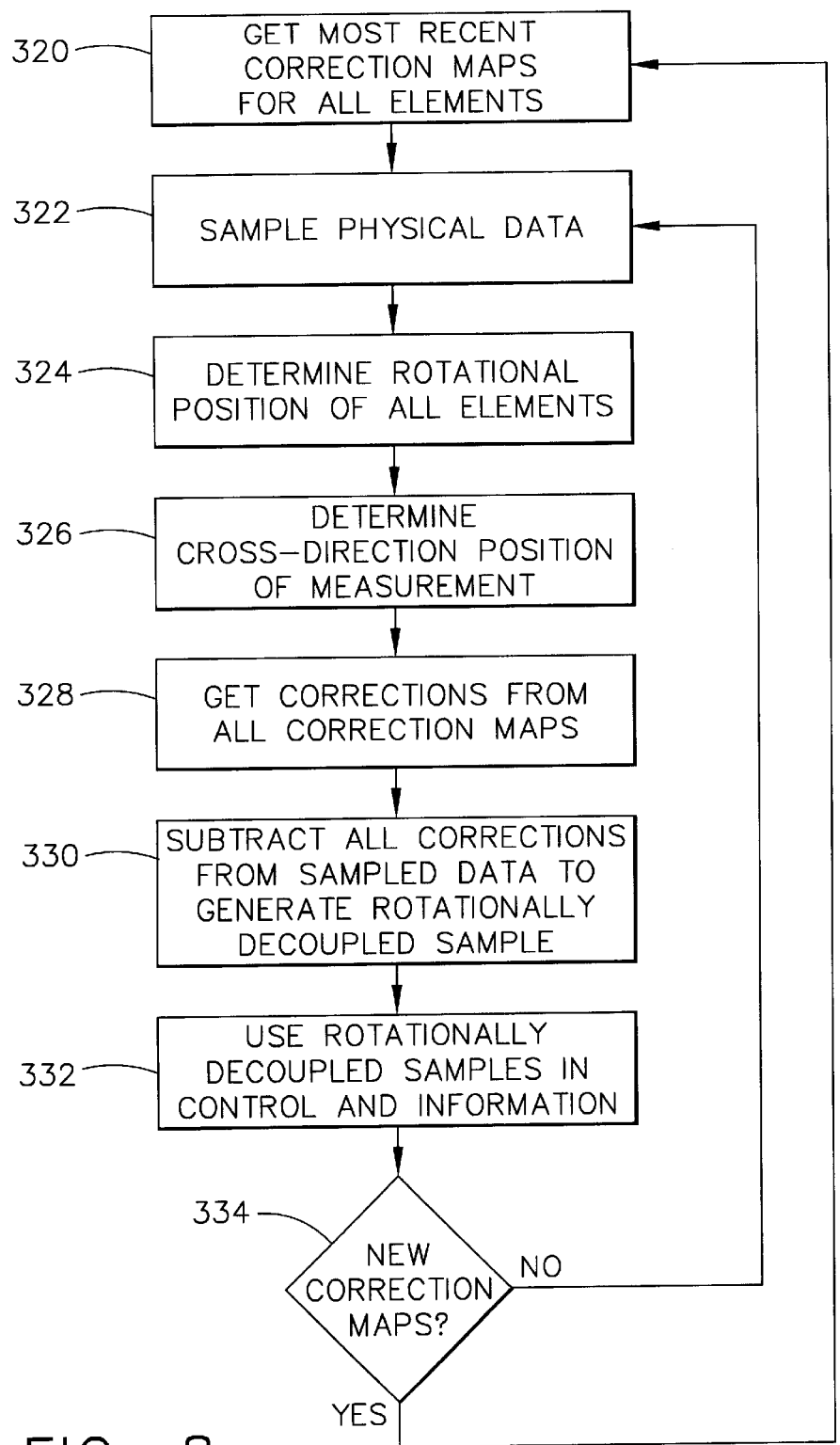
FIG. 8 is a flow chart of some of the important steps performed in real-time measurement correction, as according to the principles of the present invention.

After the valid Correction Maps or correction matrices have been calculated for all elements in the system, they must be downloaded into or otherwise made available to the process control system to be used for real time corrections. FIG. 8 is a flow chart depicting some of the important functional steps that are required to perform real time measurement correction. Starting with a step 320, the system accesses the most recent Correction Maps for all elements. (It will be understood that "all elements" means all of the rotating elements that include some type of event trigger.)

In real time, as the process control system is operating, the physical data is sampled at a step 322. This performs the identical operations that were performed in the step 300 of FIG. 7, in which sensors measure the properties of the two-dimensional moving sheet or web of material. The measurements are converted into discrete samples of data at a relatively fast collection speed.

A step 324 now determines the rotational position of all elements, essentially performing the same functions as the step 302 on FIG. 7. Again, if "m" rotational positions are used in the map, then the rotational position of each element must be converted to a number from 1 to m.

A step 326 now determines the cross-direction position of measurement, essentially performing the same functions as the step 304 in FIG. 7. If the CD axis of the map is broken into "n" positions, the CD position must be converted to a number from 1 to n.

A step 328 now obtains corrections from all of the Correction Maps that are now available for the process control system. The cross-direction position is now known (from 1 to m), as is the rotational position for each element (from 1 to n for each element). Using this information, a correction value can be determined for each element, and these corrections are the cell values of the Correction Maps.

It will be understood that the term "cell" or "measurement cell" refers to element values of a matrix for use in the present invention. Of course, a one-dimensional matrix could be used, which would then just be a series of numbers that would appear on a chart to have only a single direction. For maximum potential in using the present invention, however, the matrix would always have at least two dimensions. Of course, in highly advanced process control systems, it would be possible to use three-dimensional matrices, or even matrices of a higher order. The use of a three-dimensional matrix could provide substantial results in a system where a property at the depth of the moving web of material is one of the parameters being measured by the sensors.

A step 330 now subtracts all corrections from the sampled data to generate rotationally decoupled samples. Since the individual cell values from the Correction Maps describe the measurement error caused by rotating elements, the act of subtracting this error will correct the measured readings to produce corrected readings that can be relied upon by the process control system. The derived value is equivalent to what the sampled value would have been if the rotating elements were not impacting the original sensor measurements.

As an example, if the Correction Map contained a value of 0.3 in a particular matrix element (or measurement cell), and the real time sensor reading for the coating weight in pounds per ream at a particular coating station was 6.3 pounds per ream, then the corrected value would then be 6.3−0.3=6.0 pounds per ream. This would have been the actual sensor reading if not for the impact of the rotating elements in the process control line. Of course, a different correction value will likely be placed into adjacent matrix elements (or measurement cells), since each Cross Direction and Machine Direction position will likely be affected by a different extent when considering the effect of the rotating elements.

A step 332 now uses these rotationally decoupled samples for process control and for other information purposes. These corrected values should now be used instead of the raw sampled values, and the result will be less noisy measurements and profiles that are not influenced by rotating equipment, or by other types of periodically operating equipment (which could be non-rotating).

The logic flow now reaches a decision step 334 which determines if a "new" Correction Map is available for a particular rotating element in the process control line. The process of building new Correction Maps is continuous in the preferred embodiment of the present invention. When a new map is completed and declared valid, the newly generated map should be used. In normal circumstances, the new Correction Map will differ from the old Correction Map only slightly, and this process will slowly correct for gradual wear and other changes. Occasionally, the change may be abrupt, in response to a manual adjustment or an equipment malfunction or replacement.

Figure 9:
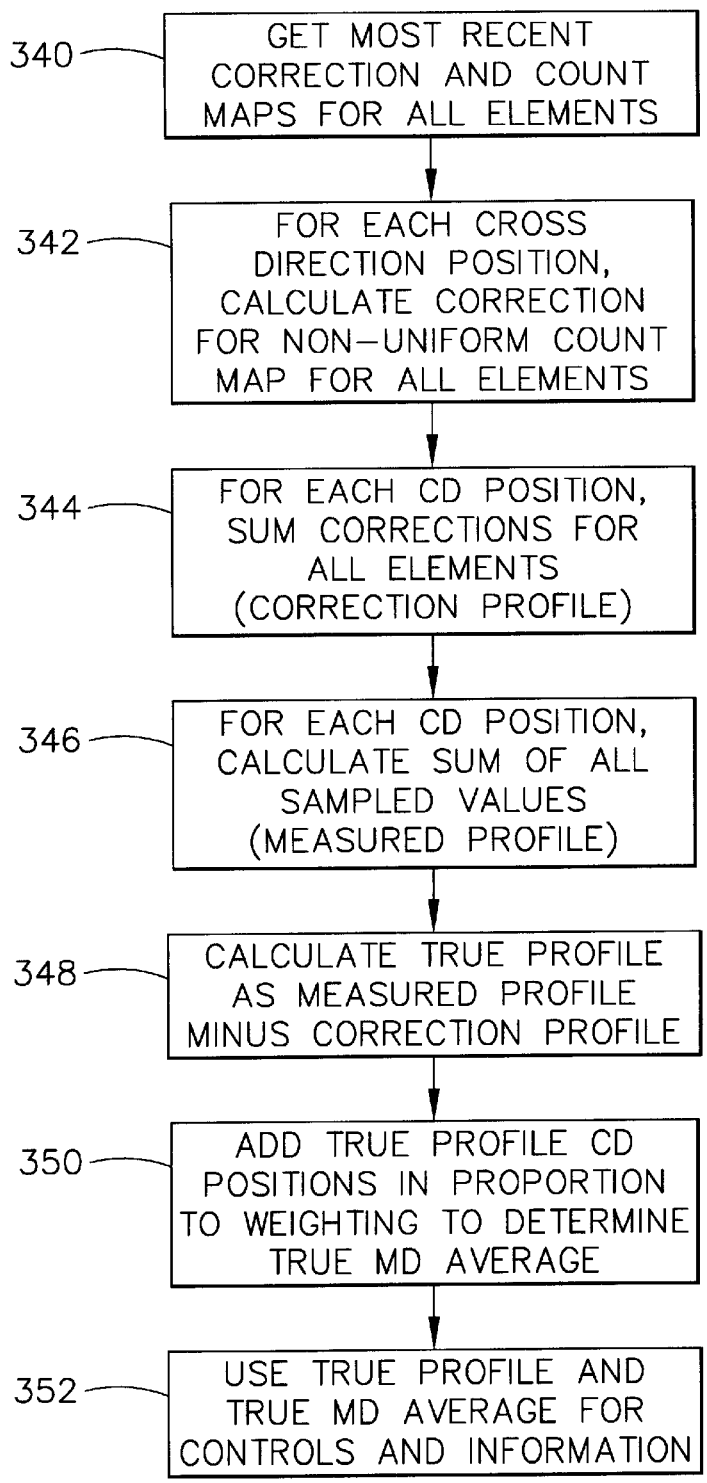
FIG. 9 is a flow chart of some of the important steps performed in non-real time measurement correction, as according to the principles of the present invention.

The present invention can also be used in non-real time measurement correction situations for process control equipment. FIG. 9 is a flow chart showing some of the important functional steps that will occur in this non-real time methodology. Starting with a step 340, the most recent Correction Maps and Count Maps are read into the process control system for all elements (i.e., all elements having triggers).

In the sampling method generally used in moving web product manufacturing process control systems (as per the data sampling system illustrated in FIG. 2), each measurement cell in a CD position affects the profile for an equal time; however, the method of sampling described above may weight certain measurement cells much more than others. Therefore, this sampling is not uniform.

This non-uniformity can be corrected by first calculating the average value for each CD position as if all measurement cells were equally sampled. Then the average value for each CD position is calculated based upon the actual sampling. The difference between these two values (i.e., between the "equal weighted sample" average and the actual value's average) per CD position provides a correction value (or correction factor) that can remove the effect of the non-uniform sampling.

A minimum number of samples is required for each measurement cell to insure that the cell average is statistically valid. The determination of this minimum number is part of the installation and setup procedure (as described hereinabove).

A step 344 now sums corrections for all elements for each CD position. This produces a "Correction Profile." At each CD position, the total correction is the sum of the corrections for all elements.

A step 346 now calculates the sum of all sampled values for each CD position, which produces a "Measured Profile." When the Correction Maps and Count Maps were generated, many samples were collected for each CD position. The Measured Profile is the average of all of these samples at each position.

A step 348 now calculates a "True Profile." Using matrix math, the Measured Profile minus the Correction Profile gives the result that is designated as the "True Profile." This will yield the actual or "true" profile during the time in which the maps were originally collected. The True Profile is not impacted by non-uniform sampling.

Non-uniform sampling can affect the MD estimates as well as the CD estimates. Once the True Profile has been calculated (as in step 348), the true MD average can be determined by averaging all CD positions in the True Profile. If all CD positions represent equal scan time divisions, a simple non-weighted average will yield the MD average; otherwise, the CD positions must be weighted according to their percentage of scan time. This "true MD average" will remove any aliases that can affect the MD measurement. A step 350 adds the True Profile CD positions in proportion to the scan time percentage weightings to determine the true MD average.

A step 352 is the culmination of this non-real time measurement correction, and the True Profile and the true MD average will be used at this step 352 in the process control system for controlling and for generating other information. While non-real time corrections will result in relatively slow control actions, if the real time corrections are not available, the slower corrections that are accurate (according to this aspect of the present invention) are far better than speedy corrections that are inaccurate.

It will be understood that the logical operations described in relation to the flow charts of FIG. 7–9 can be implemented using sequential logic, such as by using microprocessor technology or using a logic state machine; it even could be implemented using parallel logic. The preferred embodiment uses a microprocessor to execute software instructions that are stored in memory cells within a memory device.

It will be further understood that the precise logical operations depicted in the flow charts of FIGS. 7–9, and discussed hereinabove, could be somewhat modified to perform similar, although not exact, functions without departing from the principles of the present invention. The exact nature of some of the decision steps and other commands in these flow charts are directed toward specific paper mill applications, and certainly similar, but somewhat different, steps would be taken for use with other types of material producing systems in many instances, although the overall inventive results would be the same.

Figure 10:
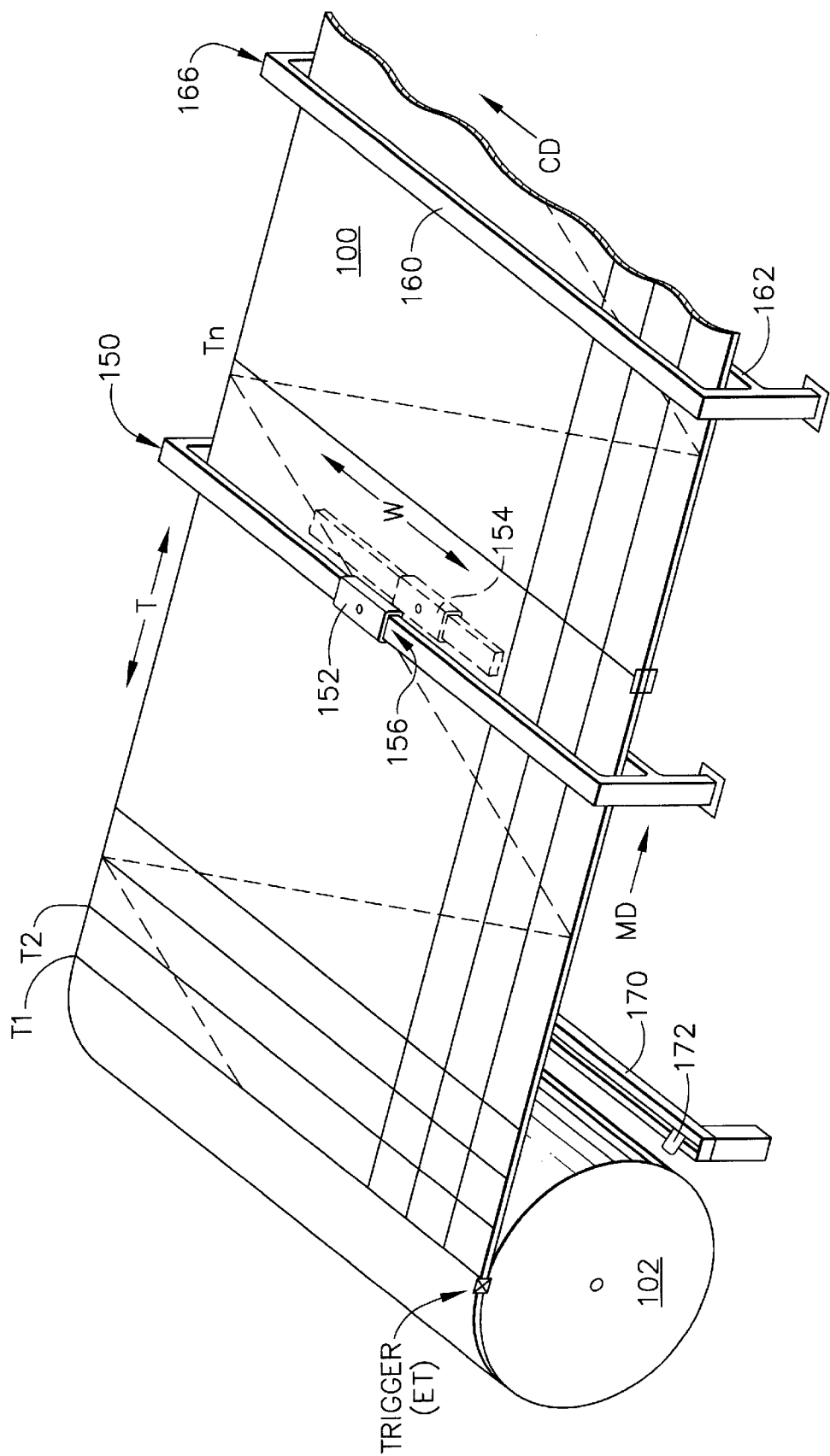
FIG. 10 is a perspective view of an alternative embodiment used in conjunction with the process control line of FIG. 1, and illustrates various types of web scanners and roll scanners.

Some alternative sensing mechanisms that may used in conjunction with the present invention are now described, in reference to FIG. 10. Using conventional sensing techniques, the properties of the two-dimensional sheet or web are most commonly measured with a scanner which transports a sensor across the sheet. Such a scanner will typically have a frame 150, which contains a moving carriage 156 having a top head 152 and a bottom head 154, which must be kept in alignment while scanning. In some measurement technologies, one of the heads will contain an energy source (nuclear, x-ray, infrared, etc.) for the measurement, while the other head will contain a receiver for measuring (detecting) the energy.

It will be understood that a typical scanner frame (such as frame 150) will include a support services package. This support services package provides, for example, water, pressurized air (or a vacuum), and electrical power, as appropriate for the entire scanner unit. Certainly there will also be electrical signal wiring that carries the output signals from the sensing heads 152 and 154. Since the movable scanning heads 152 and 154 are single-channel units, there would be only two output signals, and those could perhaps be multiplexed at the frame 150 to reduce the number of electrical conductors.

For thickness or caliper measurement, top and bottom heads are also needed to measure the gap between a probe contacting the sheet (or riding on an air bearing) and a reference on the other side. Other sensors are single-sided and depend upon the scattering or reflection of the energy source, and thus need only one head, which can optionally be mounted on scanners having only one head (e.g., either head 152 or 154). All of these above sensing measurements move a single sensor across the sheet (in the cross direction) and perform all measurements of a property across the sheet using this single sensor, but at different times.

Another sensing technology option is the use of a multi-channel stationary sensor. This sensor may have both a top head 160 and bottom head 162 that covers the entire width of the sheet, or may only have a single head on one side (that covers the entire sheet width), on a frame 166. The sheet properties are measured by a plurality of sensors or channels at fixed positions across the sheet. This arrangement allows for parallel processing of the information so that in a short time interval all channels across the width can be read at once. Consequently, at each time interval in the data collection a plurality of cells in the Sum and Count Matrices must be updated, instead of a single cell as in the case of scanning sensors.

It will also be understood that a multi-channel scanner unit or frame 166 that holds the stationary sensing heads 160 and 162 will require some type of support services package. As discussed above (in reference to the moving scanner on frame 150) this alternative support services package provides, for example, water, pressurized air (or a vacuum), and electrical power, as appropriate for the entire scanner unit. Certainly there will also be electrical signal wiring that carries the output signals from the sensing heads 160 and 162.

Since the stationary sensing heads 160 and 162 are each multi-channel units, there will either be a large number of electrical conductors needed to carry the multiple output signals per head, or a significant multiplexing and/or data storing operation must take place at the sensing frame 166 to reduce the number of electrical conductors carrying the output signals. Of course, a serial output could be used for each stationary sensing head 160 and 162, which means that data samples would likely be temporarily stored in a computer memory circuit before being transmitted to an external controller or data processing device.

Another sensing technology option is to move the location of the scanning or multi-channel sensors from the sheet (or web) to one of the rotating elements affecting the sheet/web. In FIG. 10, a different frame 170 is positioned to measure a property of the roll 102 with a single scanning head 172 (that moves across the entire width of the roll 102). Examples of the measured property include: the mechanical run-out of the roll, or the thickness of a coating on the roll surface. Of course, a non-moving scanning head (not shown) could be alternatively provided that measures across the entire width of the roll 102.

Sensing of the roll position is accomplished with the mounting of a single mark (such as the trigger ET) to the roll, and then sensing (e.g., optically, magnetically, etc.) every time the mark returns to the same position. The MD position of the roll is commonly determined by time division of the total rotational time into the desired number of time divisions that are used for the time synchronized data collection. An alternative sensing option is to place a plurality of marks on the rotating element (e.g., the roll 102) at fixed rotational intervals and use the detection of these marks to determine the rotational position of the roll.

A further alternative measuring methodology is to take measurements of the roll 102 at a time when the roll is dismounted from the process line. This could take place, for example, on a test stand where ambient and operating conditions could be precisely controlled. These "off-line" measurements could include, for example, the run-out of the roll, and/or the thickness of a coating on the roll.

It will be understood that, of all the various scanning devices illustrated on FIG. 10, it would be normal to use only a single one of these scanners on a job site for a particular process line. While it would be possible to include more than one scanner on a single web process line, it may be redundant to do so when using the principles of the present invention. If more than one scanning device were to be installed on a single web process line, then it likely would be to include both a web scanner (such as the web scanner 152 and 154, or 160 and 162) and a roll scanner (such as the roll scanner 172). It would be less likely to install both a moving web scanner (such as 152 and/or 154) and a stationary web scanner (such as 160 and/or 162), since these web scanners essentially measure the same properties (i.e., having to do with the web, not the roll). It is not impossible to have two different web scanners on a single web process line, but it may not be at all cost-effective.

A further alternative for taking measurements of the web of material 100 is to use an "off-line" procedure where the movements of the web are made in steps, rather than in a continuous motion of rotational movement by the rolls. In this stepping mode of operation, the web scanner (e.g., either the moving scanner 152 or the stationary scanner 160) could take more precise readings at more slowly changing conditions. Of course, this stepping mode is only useful to accumulate readings of the web and its associated rolls before production is commenced.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A computerized process control system, adapted for use with a process equipment line having at least one moving element that moves with a time periodicity that may vary for successive cycles of movement, said process equipment line being used to produce a material which, for at least one stage of production, forms a moving web of said material that is proximal to one or more of said at least one moving element;

said process control system being characterized by:

(a) a memory circuit for storing information, at least one input device that measures at least one process parameter of said moving web of material, and a processing circuit that controls a flow of information between said memory circuit and said at least one input device;

(b) said processing circuit being configured to receive data from said at least one input device by measuring and numerically quantifying said at least one process parameter during multiple cycles of movement of said at least one moving element and store the numerically quantified information in said memory circuit, then to generate at least one correction function containing the numerically quantified information acquired over a predetermined time interval and to store said correction function in said memory circuit; and (c) said processing circuit being further configured to, during a manufacturing operation, (i) again measure and numerically quantify said at least one process parameter in substantially real time, (ii) determine positions of said at least one moving element, (iii) apply said at least one correction function to said at least one process parameter that is measured in substantially real time to generate at least one decoupled sample of said at least one process parameter and store said at least one decoupled sample in said memory circuit; (iv) and utilize said at least one decoupled sample of said at least one process parameter to operate said process equipment line, thereby providing a substantially real time measurement correction of product quality variability in said process equipment line.

2. The computerized process control system as recited in claim 1, wherein said at least one moving element comprises at least one rotating element, and said at least one decoupled sample is rotationally decoupled.

3. The computerized process control system as recited in claim 2, wherein said correction function represents matrix elements in the form of:

$$c[i_k j_k k]$$

wherein, k designates said at least one moving element, $i_k$ is the current rotational position for element k, and $j_k$ is the current cross directional position for element k.

4. The computerized process control system as recited in claim 1, wherein said moving web of said material comprises an elongated web of material being formed into a roll of paper.

5. The computerized process control system as recited in claim 1, wherein said at least one correction function is generated under control of said processing circuit by: measuring and numerically quantifying samples of physical data, and determining positions of said at least one moving element at the same sampling times; building and updating a sum function and a count function for each of said at least one moving element; determining if enough data samples have been taken to provide sufficient accuracy of said sum function and count function; building an average function for each of said at least one moving element; and building said correction function for each of said at least one moving element.

6. The computerized process control system as recited in claim 1, wherein said memory circuit comprises one of: a non-volatile electronic storage device, an optically-operated storage device, or a magnetically-operated storage device.

7. A method for substantially real time measurement correction of product quality variability in a process equipment line, said method comprising:

(a) providing a process equipment line having at least one moving element that moves with a time periodicity that may vary for successive cycles of movement, and providing a moving quantity of material that is produced using said at least one moving element;

(b) providing a processing circuit, a memory circuit to store data, and at least one input device that measures at least one process parameter of said moving material;

(c) during multiple cycles of movement of said at least one moving element, measuring and numerically quantifying said at least one process parameter, then building at least one Correction Map containing the numerically quantified information acquired over a predetermined time interval;

(d) during a manufacturing operation, (i) again measuring and numerically quantifying said at least one process parameter in substantially real time, (ii) determining positions of said at least one moving element, (iii) applying said at least one Correction Map to said at least one process parameter that is measured in substantially real time to generate at least one decoupled sample of said at least one process parameter; (iv) and utilizing said at least one decoupled sample of said at least one process parameter to operate said process equipment line.

8. The method as recited in claim 7, wherein said at least one input device comprises a scanning sensor that moves across substantially an entire width of said moving material in a cross direction while taking measurements.

9. The method as recited in claim 7, wherein said at least one input device comprises a stationary sensor that takes measurements across substantially an entire width of said moving material in a cross direction.

10. The method as recited in claim 7, wherein said at least one input device takes readings by stepping said moving material through its movements while said process equipment line is off-line.

11. The method as recited in claim 7, wherein said at least one moving element comprises at least one rotating element, and said at least one decoupled sample is rotationally decoupled.

12. The method as recited in claim 8, wherein said at least one input device comprises a scanning sensor that moves across substantially an entire width of said at least one rotating element in a cross direction while taking measurements.

13. The method as recited in claim 12, wherein said measurements are taken while off-line, and said at least one rotating element is dismounted.

14. The method as recited in claim 12, wherein said scanning sensor measures one of: (a) a run-out of said at least one rotating element, or (b) a thickness of a coating on said at least one rotating element.

15. The method as recited in claim 11, wherein said Correction Map represents matrix elements in the form of:

$$c[i_k j_k k]$$

wherein, k designates said at least one moving element, $i_k$ is the current rotational position for element k, and $j_k$ is the current cross directional position for element k.

16. The method as recited in claim 15, wherein said step of applying the at least one Correction Map to said at least one process parameter is quantified by the following expression:

$$Y = X - \sum_{k=1}^{n} C[i_k j_k k]$$

wherein,

X represents all measured readings that have been collected, and

Y represents values of time synchronized measurement correction.

17. The method as recited in claim 7, wherein said moving quantity of material comprises an elongated web of material being formed into a roll of paper.

18. The method as recited in claim 7, wherein said step of building at least one Correction Map comprises: measuring and numerically quantifying samples of physical data, and determining positions of said at least one moving element at the same sampling times; building and updating a Sum Map and a Count Map for each of said at least one moving element; determining if enough data samples have been taken to provide sufficient accuracy of said Sum Map and Count Map; building an Average Map for each of said at least one moving element; and building said Correction Map for each of said at least one moving element.

19. A computerized method for building a Correction Map for use in a system including at least one rotating element having an associated moving web of material, said method comprising:

(a) sampling physical data by use of at least one input device that measures at least one process parameter of said moving web of material;

(b) determining a rotational position of each sample for each of said at least one rotating element that is being monitored;

(c) determining a cross-directional position of each sample of said physical data;

(d) updating a Sum Map and a Count Map for each of said at least one rotating element, using said sampled physical data;

(e) determining if a sufficient amount of sampled physical data has been acquired for convergence to an appropriately small tolerance and, if NO sampling further physical data, or if YES building an Average Map for each of said at least one rotating element; and (f) building a Correction Map for each of said at least one rotating element, said Correction Map containing a plurality of numeric values related to irregularities in said at least one rotating element.

20. The computerized method as recited in claim 19, wherein said step of building a Correction Map comprises generating a matrix having elements in the form of:

$$C[i_k j_k k]$$

wherein, k designates said at least one moving element, $i_k$ is the current rotational position for element k, and $j_k$ is the current cross directional position for element k.

21. The computerized method as recited in claim 19, wherein said step of determining rotational positions of said at least one rotating element comprises: iteratively measuring data to produce data samples that correspond to a physical parameter of one of said at least one rotating elements so that a plurality of said iterative measurements are acquired at varying positions of said one of said at least one rotating elements.

22. The computerized method as recited in claim 21, wherein said step of determining a cross-directional position of each sample of said physical data comprises: measuring a position in the cross-direction of each of said iteratively measured data samples.

23. The computerized method as recited in claim 19, wherein said Sum Map is generated by: placing a first numeric quantity into a matrix having individual matrix elements, said matrix elements having a row and column position that corresponds to a rotational position and a cross-directional position, said first numeric quantity being related to the sum of acquired data measurements of said physical data by way of said at least one input device for a particular matrix element position during said step of sampling physical data.

24. The computerized method as recited in claim 23, wherein said Count Map is generated by: placing a second numeric quantity into a matrix having individual matrix elements, said matrix elements having a row and column position that corresponds to a rotational position and a cross-directional position, said second numeric quantity being related to the number of samples that have been acquired for a particular matrix element position during said step of sampling physical data.

25. The computerized method as recited in claim 24, wherein said Average Map is generated by: dividing said first numeric quantity by said second numeric quantity for each corresponding matrix element of said Sum Map and said Count Map.

26. The computerized method as recited in claim 19, wherein said convergence to an appropriately small tolerance comprises: determining when each matrix element converges to a numeric value within a predetermined tolerance of its value after a theoretical infinite collection time.

27. The computerized method as recited in claim 19, wherein said at least one rotating element that is being monitored comprises a rotating element that is tied to a trigger.

28. A computerized method for controlling in substantially real time a system including at least one rotating element having an associated moving web of material, said method comprising:

(a) providing a control system for controlling said at least one rotating element;

(b) providing a Correction Map for each of said at least one rotating element;

(c) acquiring a plurality of physical data samples by use of at least one input device that measures at least one process parameter of said moving web of material;

(d) determining rotational positions for each of said at least one rotating element that is being monitored, for each of said plurality of physical data samples;

(e) determining a cross-directional position of each sample of said physical data;

(f) using said Correction Map, looking up a correction value for each of said at least one rotating element;

(g) generating rotationally decoupled values in substantially real time by applying said correction value to one of said plurality of physical data samples; and (h) applying said rotationally decoupled values to said control system.

29. The computerized method as recited in claim 28, further comprising: determining if a revised Correction Map is available; if not return to acquiring a plurality of physical data samples; if so, return to providing a Correction Map for each of said at least one rotating element.

30. The computerized method as recited in claim 28, wherein said at least one rotating element that is being monitored comprises a rotating element that is tied to a trigger.

31. The computerized method as recited in claim 28, wherein the step of generating rotationally decoupled values in substantially real time comprises: subtracting said Correction Map from said plurality of physical data samples.

32. A method for correction of product quality variability of a moving web of material in a process equipment line, said method comprising:
   (a) providing a process equipment line having at least one moving element that moves with a time periodicity that may vary for successive cycles of movement, and providing a moving web of material that is produced using said at least one moving element;
   (b) providing a processing circuit, a memory circuit, and at least one input device that measures at least one process parameter of said moving web of material;
   (c) during multiple cycles of movement of said at least one moving element, measuring and numerically quantifying said at least one process parameter, then building a Correction Map containing the numerically quantified information acquired over a predetermined time interval;
   (d) determining, for each web cross direction position, a correction for non-uniformity in a Count Map, for all of said at least one moving element;
   (e) creating a Correction Profile by summing, for each web cross direction position, said corrections for all of said at least one moving element;
   (f) creating a Measured Profile by averaging samples of the numerically quantified information taken at each cross direction position over said predetermined time interval;
   (g) creating a True Profile by subtracting said Correction Profile from said Measured Profile;
   (h) determining a True Machine Direction Average by averaging cross direction positions of said True Profile; and
   (i) controlling said process equipment line using said True Profile and said True Machine Direction Average as corrected values.

33. The method as recited in claim 32, wherein said step of building at least one Correction Map comprises: measuring and numerically quantifying samples of physical data, and determining positions of said at least one moving element at the same sampling times; building and updating a Sum Map and a Count Map for each of said at least one moving element; determining if enough data samples have been taken to provide sufficient accuracy of said Sum Map and Count Map; building an Average Map for each of said at least one moving element; and building said Correction Map for each of said at least one moving element.

34. The method as recited in claim 32, wherein said step of determining a True Machine Direction Average further comprises: when averaging all cross direction positions in said True Profile, (a) if all cross direction positions represent equal scan time divisions, use a simple non-weighted average, or (b) if not, weight the cross direction positions according to their percentage of scan time.

35. The method as recited in claim 32, wherein said at least one rotating element that is being monitored comprises a rotating element that is tied to a trigger.

36. A computerized process control system, adapted for use with a system having at least one rotating element and an associated moving web of said material; said process control system being characterized by:
   (a) a memory circuit for storing information, at least one input device that measures at least one process parameter of said moving web of material, and a processing circuit that controls a flow of information between said memory circuit and said at least one input device, said memory circuit containing a correction function for each of said at least one rotating element;
   (b) said processing circuit and said at least one input device being configured: (i) to acquire a plurality of physical data samples, (ii) to determine rotational positions for each of said at least one rotating element that is being monitored, for each of said plurality of physical data samples, and (iii) to determine a cross-directional position of each sample of said physical data; and
   (c) said processing circuit and said memory circuit being configured: (i) to look up a correction value, using said correction function, for each of said at least one rotating element, (ii) to generate rotationally decoupled values in substantially real time by applying said correction value to one of said plurality of physical data samples, and (iii) to apply said rotationally decoupled values to said control system.

37. The computerized process control system as recited in claim 36, wherein said at least one rotating element that is being monitored comprises a rotating element that is tied to a trigger.

38. The computerized process control system as recited in claim 36, wherein said generated rotationally decoupled values are determined by subtracting said correction function from said plurality of physical data samples.

39. A computerized process control system, adapted for use with a process equipment line having at least one moving element that moves with a time periodicity that may vary for successive cycles of movement, and which is used with an associated moving web of said material;
   said process control system being characterized by:
   (a) a memory circuit for storing information, at least one input device that measures at least one process parameter of said moving web of material, and a processing circuit that controls a flow of information between said memory circuit and said at least one input device;
   (b) said processing circuit and said at least one input device being configured: (i) to measure and numerically quantify said at least one process parameter during multiple cycles of movement of said at least one moving element, and (ii) to generate a correction function containing the numerically quantified information acquired over a predetermined time interval;
   (c) said processing circuit being further configured: (i) to determine, for each web cross direction position, a correction for non-uniformity in a count function, for all of said at least one moving element, (ii) to create a Correction Profile by summing, for each web cross direction position, said corrections for all of said at least one moving element, (iii) to create a Measured Profile by averaging samples of the numerically quantified information taken at each cross direction position over said predetermined time interval, (iv) to create a True Profile by subtracting said Correction Profile from said Measured Profile, and (v) to determine a True Machine Direction Average by averaging cross direction positions of said True Profile; and (d) said processing circuit being still further configured to control said process equipment line using said True Profile and said True Machine Direction Average as corrected values.

40. The computerized process control system as recited in claim 39, wherein the procedure for generating said at least one correction function comprises: measuring and numerically quantifying samples of physical data, and determining positions of said at least one moving element at the same sampling times; building and updating a sum function and a count function for each of said at least one moving element; determining if enough data samples have been taken to provide sufficient accuracy of said sum function and count function; building an average function for each of said at least one moving element; and generating said correction function for each of said at least one moving element.

41. The computerized process control system as recited in claim 39, wherein the procedure for determining a True Machine Direction Average further comprises: when averaging all cross direction positions in said True Profile, (a) if all cross direction positions represent equal scan time divisions, use a simple non-weighted average, or (b) if not, weight the cross direction positions according to their percentage of scan time.

42. The computerized process control system as recited in claim 39, wherein said at least one rotating element that is being monitored comprises a rotating element that is tied to a trigger.

* * * * *